(12) United States Patent
Nakamura et al.

(10) Patent No.: US 7,273,488 B2
(45) Date of Patent: Sep. 25, 2007

(54) HIGH-RIGIDITY FORCEPS TIP ASSEMBLY FOR ACTIVE FORCEPS AND ACTIVE FORCEPS EQUIPPED WITH THE SAME

(75) Inventors: Yoshihiko Nakamura, Edogawa-ku (JP); Masafumi Okada, Bunkyo-ku (JP); Shingo Chiyoda, Machida (JP)

(73) Assignee: The University of Tokyo, Tokyo (JP)

( * ) Notice: Subject to any disclaimer, the term of this patent is extended or adjusted under 35 U.S.C. 154(b) by 608 days.

(21) Appl. No.: 10/455,355

(22) Filed: Jun. 6, 2003

(65) Prior Publication Data

US 2004/0111113 A1    Jun. 10, 2004

(30) Foreign Application Priority Data

Dec. 9, 2002    (JP)    ............................. 2002-356971

(51) Int. Cl.
*B25J 17/02*    (2006.01)
*A61B 17/28*    (2006.01)

(52) U.S. Cl. ................. 606/205; 74/490.05; 74/490.06

(58) Field of Classification Search ................ 600/141, 600/142, 201, 216; 606/198, 205–211, 180, 606/56, 130; 294/99.1, 99.2, 100, 106, 115; 74/490.01–490.09
See application file for complete search history.

(56) References Cited

U.S. PATENT DOCUMENTS 4,806,068 A *   2/1989   Kohli et al. ................. 414/735
5,656,905 A *   8/1997   Tsai ....................... 318/568.21
5,740,699 A *   4/1998   Ballantyne et al. ....... 74/490.06
6,330,837 B1*  12/2001   Charles et al. ........... 74/490.06
6,793,669 B2*   9/2004   Nakamura et al. .......... 606/205

FOREIGN PATENT DOCUMENTS

CA    2 376 745 A1    1/2003

* cited by examiner

*Primary Examiner*—(Jackie) Tan-Uyen Ho
*Assistant Examiner*—Kathleen Sonnett
(74) *Attorney, Agent, or Firm*—Oliff & Berridge, PLC

(57) ABSTRACT

Provided is a forceps tip assembly capable of supporting a forceps tip with high rigidity in order to realize a laparoscopic surgery requiring a significant power with the forceps tip, such as an organ removal surgery which has been heretofore difficult to be performed by a robot for medical use. The forceps tip assembly includes: a forceps tip supporting member which has a supporting part for supporting a forceps tip and three leg parts which are disposed at even intervals in a circumferential direction around a central axis line C1 and fixed to the supporting part so as to protrude backward from the supporting part; and three back-and-forth moving members which are disposed at even intervals in a circumferential direction around a predetermined central axis line C2 extending in a front-to-rear direction, which have their front end portions coupled with the three leg pads swingably and slidably in a direction orthogonal to the predetermined central axis line C2 and which are mutually coupled together as relatively movable in the extending direction of central axis line C2.

11 Claims, 8 Drawing Sheets

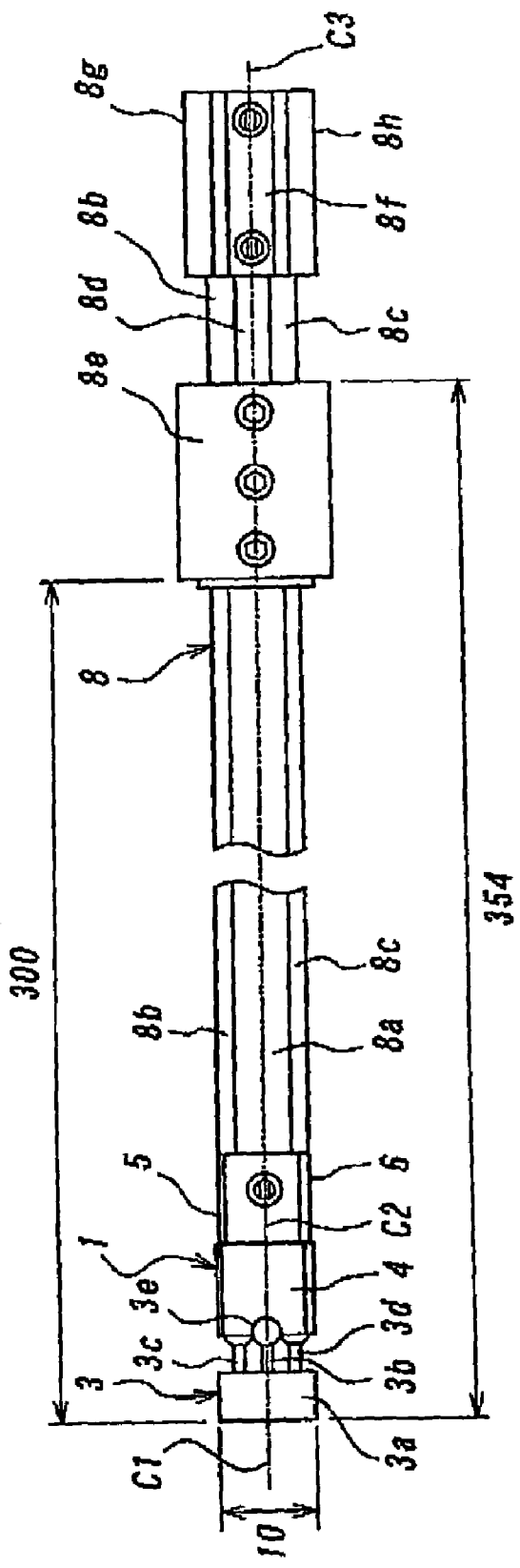
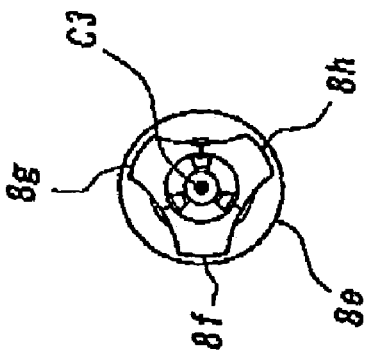
FIG. 5a
FIG. 5b

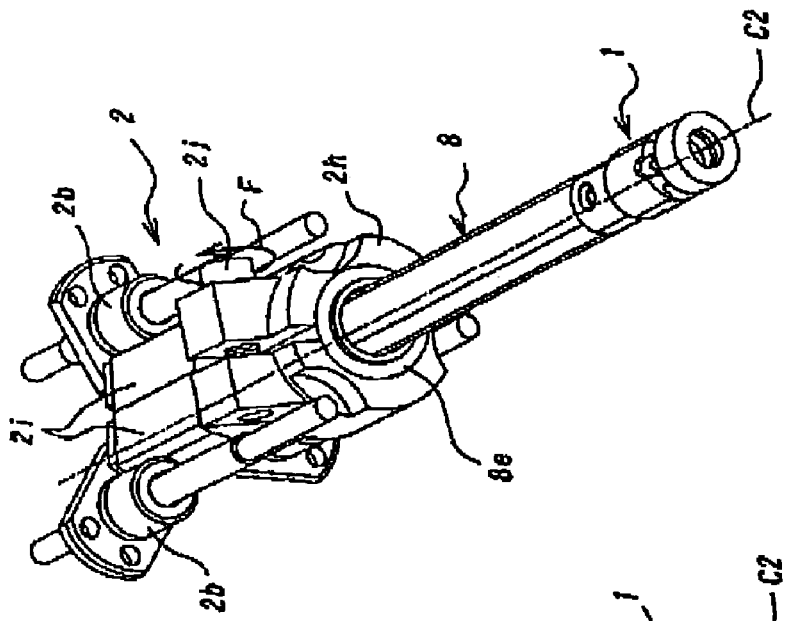
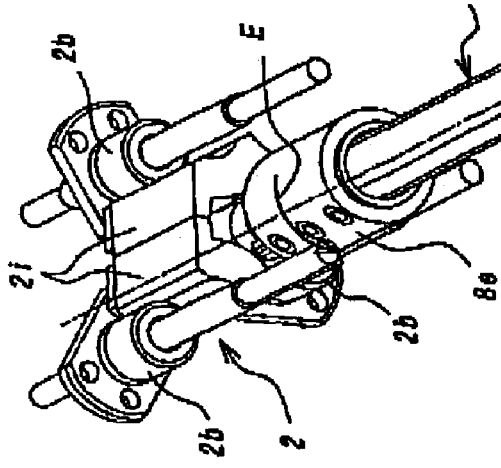
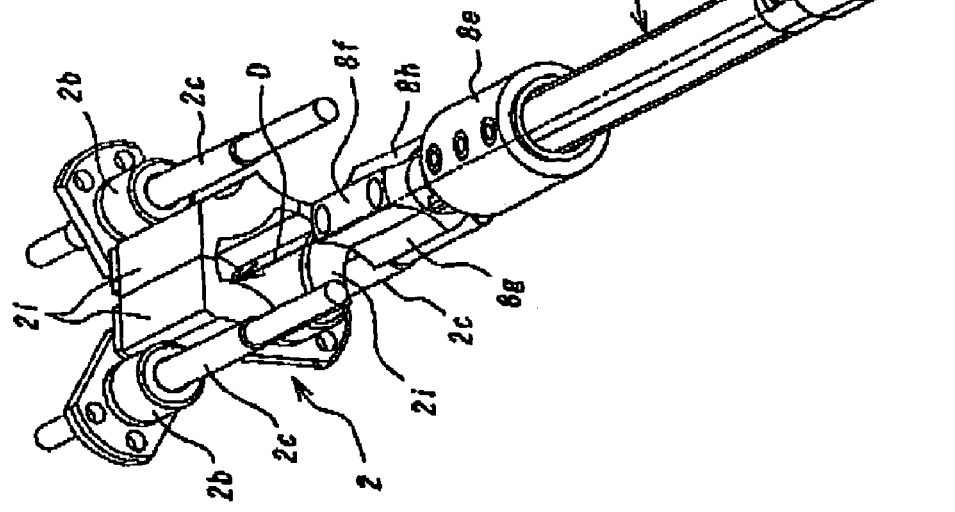

HIGH-RIGIDITY FORCEPS TIP ASSEMBLY FOR ACTIVE FORCEPS AND ACTIVE FORCEPS EQUIPPED WITH THE SAME

BACKGROUND OF THE INVENTION

1. Field of the Invention

The present invention relates to a high-rigidity forceps tip assembly for an active forceps used in a minimally invasive surgery and the like and to an active forceps including the same.

2. Prior Art

Conventional active forceps used in a master-slave robot for a minimally invasive surgery (particularly a laparoscopic surgery) is mostly ones that change a direction of a forceps tip by wire driving (for example, refer to Guthart G. S., and J. K. Salisbury, "The Intuitive Telesurgery System: Overview and Application." Proc. of the IEEE International Conference on Robotics and Automation, San Francisco Calif., April 2000). This is because a small mechanism of changing a direction of a forceps by transmitting a driving force to a forceps tip from an actuator disposed in a base of the forceps can be relatively easily realized by use of the wire driving.

In the wire driven active forceps, even if the actuator has a large driving force, a wire may be elongated or cut off because of low rigidity and durability of the wire. Thus, it is difficult to transmit a large force up to the forceps tip. Consequently, the wire driven active forceps has been used in an endoscopic surgery, such as angiorrhaphy, which does not require a very large force.

When an active forceps is used in, for example, an organ removal surgery, the active forceps has to hold an organ by its tip. Thus, it is necessary that not only an actuator has a large driving force but also the force can be efficiently transmitted to the tip of the forceps and the forceps tip is supported with high rigidity. Consequently, the conventional wire driven active forceps described above was inappropriate for the organ removal surgery.

SUMMARY OF THE INVENTION

The present invention has an object to provide a high-rigidity forceps tip assembly which advantageously resolves the foregoing problem and an active forceps including the same. A high-rigidity forceps tip assembly for an active forceps of the present invention includes: a forceps tip supporting member having a supporting part for supporting a forceps tip and three leg parts which are positioned at even intervals in a circumferential direction around a central axis line of the supporting part and are fixed to the supporting part so as to protrude backward from the supporting part, respectively; and three back-and-forth moving members which are disposed at even intervals in a circumferential direction around a predetermined central axis line extending in a front-to-rear direction, which have their front end portions coupled with the three leg parts swingably and slidably in a direction orthogonal to the predetermined central axis line and which are mutually coupled together as relatively movable in the front-to-rear direction.

In the above forceps tip assembly, to the front end portions of the three back-and-forth moving members which are disposed at even intervals in the circumferential direction around the predetermined central axis line extending in the front-to-rear direction and are mutually coupled together as relatively movable in the front-to-rear direction, the three leg parts which are positioned at even intervals in the circumferential direction around the central axis line of the support part for supporting the forceps tip and are fixed to the supporting part of the forceps tip supporting member so as to protrude backward from the supporting part, respectively, are coupled as swingable and as slidable in the direction orthogonal to the predetermined central axis line. Thus, when the three back-and-forth moving members are moved in the front-to-rear direction relatively to each other; a plane passing coupling points between the three leg parts and the front end portions of the three back-and-forth members can be swung toward an arbitrary direction from a position facing, a front orthogonal to the predetermined central axis line. Consequently, by means of the three leg parts, the supporting part can be swung toward an arbitrary direction from a reference position facing the front orthogonal to the predetermined central axis line.

Therefore, according to the forceps tip assembly of the present invention, the forceps tip mounted on the supporting part can be swung toward an arbitrary direction. Moreover, for swinging the supporting part, back-and-forth movement of the coupling points between the three leg parts and the front end portions of the three back-and-forth moving members is transmitted to the supporting part via the three leg parts which extend in parallel with a movement direction of the coupling points when the supporting part is at the foregoing reference position. Thus, a force applied to the supporting part fm the leg parts in the swinging of the supporting part is in a direction of pushing/pulling the leg parts. Consequently, rigidity of supporting the forceps tip by the supporting part can be increased.

Note that, according to the present invention, spheres formed in respective rear end portions of the three leg parts and cylindrical grooves which are formed in the respective front end portions of the three back-and-forth moving members and extend in the direction orthogonal to the predetermined central axis line may be engaged with each other as swingable and slidable. By this swingable and slidable engagement, the three leg parts may be coupled with the front end portions of the three back-and-forth moving members at swingable and as slidable in the direction orthogonal to the predetermined central axis line, respectively. With such a constitution, the engagement structure includes the spheres and the cylindrical grooves, and thus the number of movable components can be reduced. Also in this regard, the rigidity of supporting the forceps tip can be increased. Moreover, the engagement structure can be formed by easily fabricating those movable components.

Moreover, according to the present invention, the supporting part may be formed of a ring-shaped member with such a constitution, by fitting or screwing the forceps tip into a center hole of the ring-shaped supping part, the forceps tip can be easily mounted on the supporting part. Moreover, a link member for opening/closing the forceps tip can be inserted into the center hole of the supporting part and thus the forceps tip can be opened and closed strongly by the link member while minimizing the width of the forceps tip assembly.

Furthermore, according to the present invention, the three back-and-forth moving members may be coupled with each other as relatively movable in the front-to-rear direction by use of grooves and ribs. The groove and rib may form a hook-shaped cross section, which are engaged with each other as slidable in the front-to-rear direction and are hooked up with each other in a direction intersecting with the front-to-rear direction. With such a constitution, the three back-and-forth moving members are coupled with each other with high rigidity. Thus, the forceps tip can be allowed to have high rigidity with a simple constitution.

The active forceps of the present invention includes the foregoing high-rigidity forceps tip assembly for an active forceps and includes a forceps base part having: three base part side back-and-forth moving members which are integrally coupled with the three back-and-forth moving members, are coupled with each other as relatively movable in the front-to-rear direction and constitute a link mechanism together with the back-and-forth moving members and the supporting part; and a base part frame including driving means for relatively moving the base part side back-and-forth moving members in the front-to-rear direction.

According to the above active forceps, the driving means provided in the base part frame of the forceps base part moves the three base part side back-and-forth moving members of the forceps base part, which constitute the link mechanism together with the back-and-forth moving members and supporting member of the forceps tip assembly, relatively to each other in the front-to-rear direction from a reference state where the members are aligned side-by-side with each other. In response to the relative movement of those base part side back-and-forth moving members in the front-to-rear direction, the three back-and-forth moving members of the forceps tip assembly, which are integrally coupled with the base part side back-and-forth moving members and coupled with each other as relatively movable in the front-to-rear direction, are relatively moved in the front-to-rear direction. Thus, the supporting part of the forceps tip assembly moves the three leg parts, which are fixed to the supporting part so as to protrude backward from the supporting part, toward the front-to-rear direction of the back-and-forth moving members and is swung as a whole. Consequently, the forceps tip supported by the supporting part changes its direction.

Therefore, according to the active forceps of the present invention, as described above, the forceps tip assembly supports the forceps tip with high rigidity, the driving means transmits a driving force to the forceps tip via the link mechanism, and thus the direction of the forceps tip can be changed. Consequently, the driving force can be efficiently transmitted to the forceps tip and the forceps tip can have rigidity higher than that of a wire driven one. Accordingly, the active forceps can be utilized for an operation which requires strength in the forceps tip, which includes, for example, an organ removal surgery and the like. Moreover, on the forceps tip side than the forceps base part, there merely exist, primarily, the back-and-forth moving members, the supporting part, the leg parts and the forceps tip, and if necessary, linking members which integrally link the back-and-forth moving members with the base part side back-and-forth moving members. Thus, the part at the forceps tip side can be easily made to have a smaller diameter. Consequently, the active forceps enables a minimally invasive surgery in surgeries such as the organ removal surgery accompanied by an operation requiring strength in the forceps tip.

BRIEF DESCRIPTION OF THE DRAWINGS

FIG. 1b is a cross-sectional view along a plane A in FIG. 1a and FIG. 1c is an explanatory view showing an operation of a part B in FIG. 1a;

FIG. 5a is a front view showing a forceps shaft part of the active forceps of the foregoing embodiment together with the forceps tip assembly and FIG. 5b is an end view when FIG. 5a is viewed from the rear end;

FIGS. 7a to 7c are explanatory views showing a procedure of mounting the forceps shaft part on the foregoing forceps base part.

DETAILED DESCRIPTION OF THE PREFERRED EMBODIMENTS

Figure 1A:
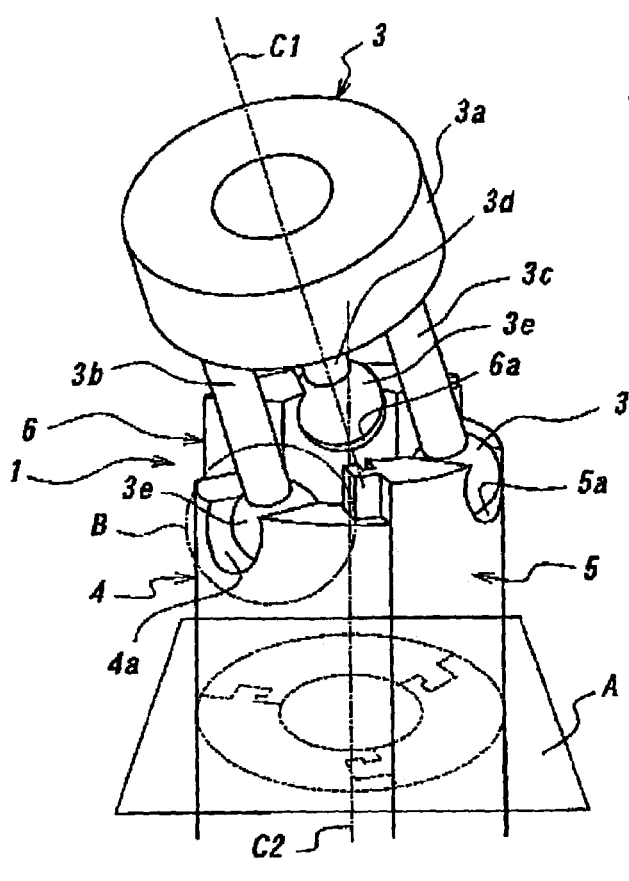
FIG. 1a is a perspective view showing an embodiment of a high-rigidity forceps tip assembly for an active forceps of the present invention.
Figure 1B:
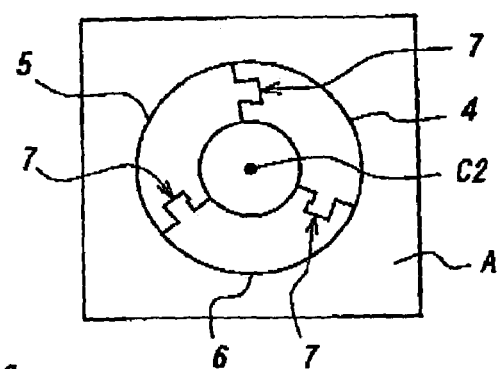
Figure 1C:
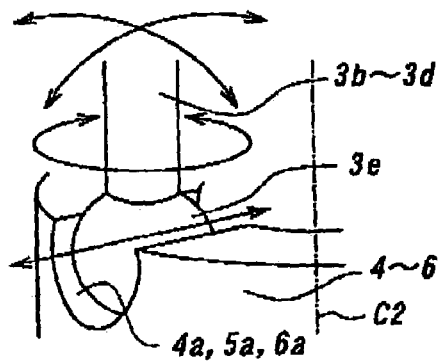
Figure 2:
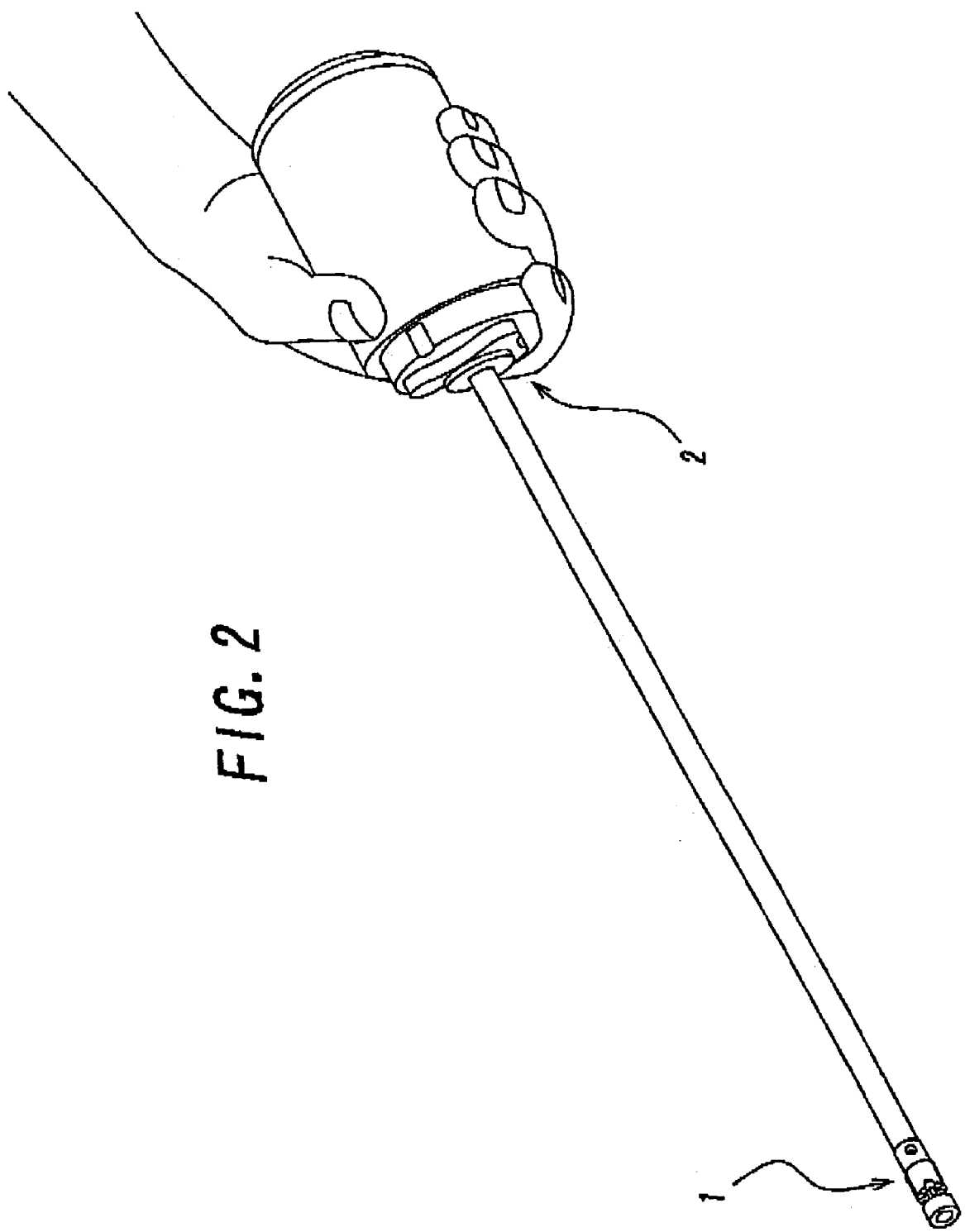
FIG. 2 is a perspective view showing an embodiment of an active forceps of the present invention, which includes the forceps tip assembly of the foregoing embodiment.

With reference to the drawings, embodiments of the present invention will be described in detail below. Herein, FIG. 1a is a perspective view showing an embodiment of a high-rigidity forceps tip assembly for an active forceps according to the present invention, FIG. 1b is a cross-sectional view along the plane A in FIG. 1a and FIG. 1c is an explanatory view showing an operation of the part B in FIG. 1a. Moreover, FIG. 2 is a perspective view showing an embodiment of an active forceps of the present invention, which includes the forceps tip assembly of the foregoing embodiment. In the drawings, reference numeral 1 denotes the forceps tip assembly of the foregoing embodiment and reference numeral 2 denotes a forceps base part.

In the forceps tip assembly 1 of this embodiment, link driving is adopted as a driving system having high rigidity. In order to realize the link driving, the forceps tip assembly 1 of this embodiment includes a tripodal forceps tip supporting member 3 as shown in FIG. 1a. This forceps tip supporting member 3 has: a supporting part 3a formed of a ring-shaped member in order to support an unillustrated forceps tip; and three leg parts 3b, 3c and 3d which are disposed around the central axis line C1 of the supporting part 3a at even intervals in a circumferential direction and are screwed into the supporting part 3a and fixed thereto so as to protrude backward from the supporting part 3a in parallel with the central axis line C1.

Moreover, the forceps tip assembly 1 of this embodiment includes three back-and-forth moving members 4, 5 and 6 which are disposed around a predetermined central axis line C2 extending in a front-to-rear direction (a vertical direction in FIG. 1a) at even intervals in a circumferential direction. Specifically, to front end portions of the back-and-forth moving members 4 to 6, the three leg parts 3b to 3d of the forceps tip supporting member 3 are coupled as swingable and as slidable in a direction orthogonal to the foregoing central axis line C2. As shown in FIG. 1b, these three back-and-forth moving members 4 to 6 are mutually coupled together as relatively slidable in the front-to-rear direction by linear movement joints 7 with a hook-shaped cross section, each of the joints including a groove and a rib which engage with each other. Thus, the three back-and-forth moving members 4 to 6 constitute a columnar shape.

Here, as shown in FIG. 1*c*, the coupling of the three leg parts 3*b* to 3*d* and the three back-and-forth moving members 4 to 6 is made by slidable engagement of spheres 3*e* integrally formed in respective rear end portions of the three leg parts 3*b* to 3*d* and cylindrical grooves 4*a*, 5*a* and 6*a* which are formed in the respective front end portions of the three back-and-forth moving members 4 to 6 and extend in the direction orthogonal to the foregoing central axis line C2. Thus, as shown in FIG. 1*c*, each of the leg parts 3*b* to 3*d* has four degrees of freedom in total, including three degrees of freedom in rotation and one degree of freedom in translation.

Figure 3:
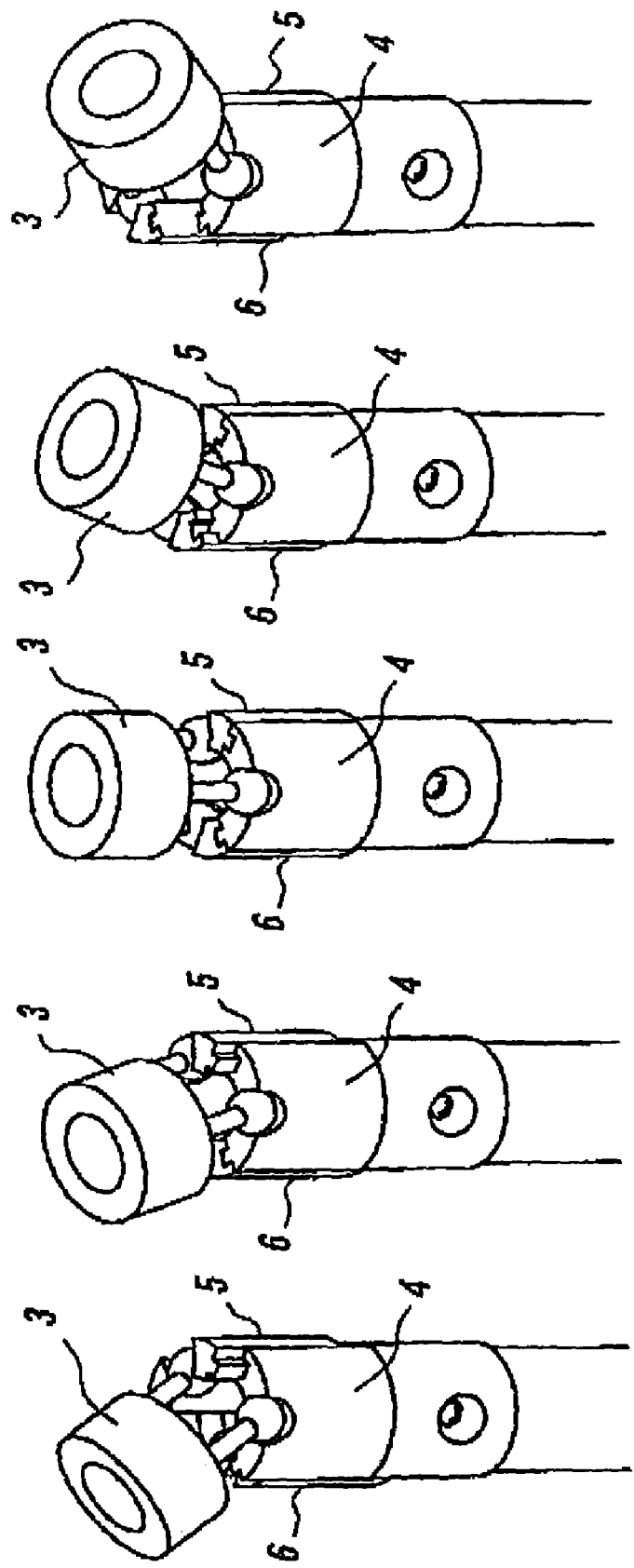
FIGS. 3a to 3e are perspective views showing an operation with two degrees of freedom in bending of a forceps tip supporting member of the forceps tip assembly of the foregoing embodiment.

According to the forceps tip assembly 1 of this embodiment, one of the three back-and-forth moving members 4 to 6 constituting the link mechanism together with the forceps tip supporting member 3 is fixed and two of the remaining back-and-forth moving members are allowed to slide independently with respect to the fixed back-and-forth moving member. Consequently, as shown in FIGS. 3*a* to 3*e*, it is possible to realize two degrees of freedom of bending of the forceps tip supporting member 3 and thus of a forceps tip fixed thereto. FIG. 3*a* shows a state where the back-and-forth moving members 4 and 6 are fixed and the back-and-forth moving member 5 is largely moved forward, FIG. 3*b* shows a state where the back-and-forth moving members 4 and 6 are fixed and the back-and-forth moving member 5 is moved a little forward, FIG. 3*c* shows a state where the three back-and-forth moving members 4 to 6 are aligned side-by-side with each other and the forceps tip supporting member 3 is set in its reference position at which the supporting part 3*a* thereof faces a front face orthogonal to the foregoing central axis line C2, FIG. 3*d* shows a state where the back-and-forth moving members 4 and 5 are fixed and the back-and-forth moving member 6 is moved a little forward and FIG. 3*e* shows a state where the back-and-forth moving members 4 and 5 are fixed and the back-and-forth moving member 6 is largely moved forward.

Furthermore, in the forceps tip assembly 1 of this embodiment, the back-and-forth movement of the spheres 3*e* as linking points of the front end portions of the three back-and-forth moving members 4 to 6 with the three leg parts 3*b* to 3*d* is transmitted to the supporting part 3*a* via the three leg parts 3*b* to 3*d* extending in parallel with the movement directions of the back-and-forth moving members 4 to 6 at the reference position of the forceps tip supporting member 3 at which the supporting part 3*a* faces the front face orthogonal to the foregoing central axis line C2, so that the supporting part is swung. Thus, a force applied to the supporting part 3*a* from the leg parts 3*b* to 3*d* in the swinging of the supporting part is in a direction of pushing/pulling the leg parts 3*b* to 3*d*. Consequently, rigidity of supporting the forceps tip by the supporting part 3*a* can be increased. Furthermore, in the forceps tip assembly 1 of this embodiment, there are only four movable components in total, including: the forceps tip supporting member 3 in which all of the supporting part 3*a*, three leg parts 3*b* to 3*d* and spheres 3*e* are integrally formed; and the back-and-forth moving members 4 to 6. Thus, the extremely small number of movable components makes it possible to realize much higher rigidity.

Figure 4:
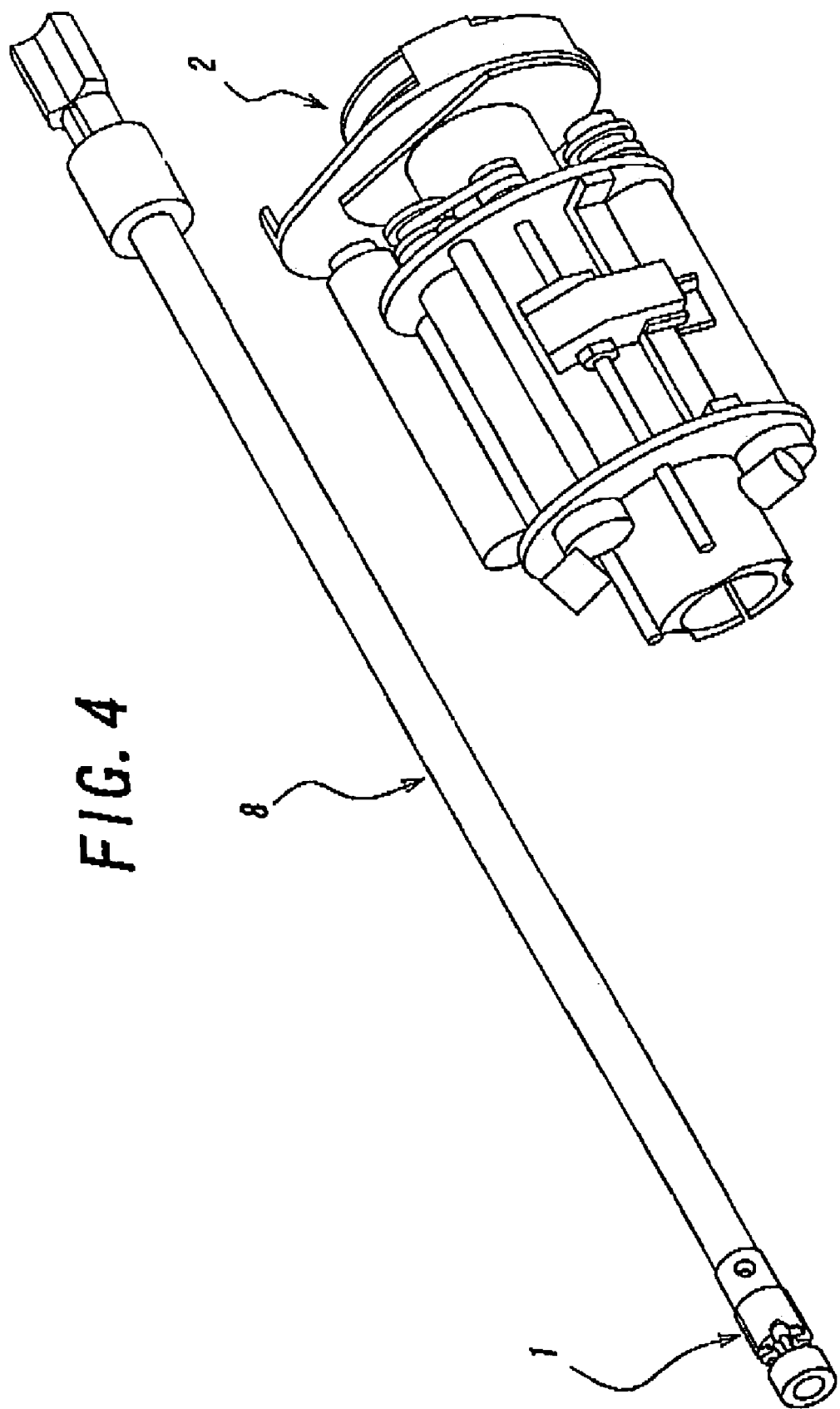
FIG. 4 is an exploded perspective view showing the active forceps of the foregoing embodiment.

Meanwhile, as shown in an exploded view of FIG. 4, the active forceps of the foregoing embodiment further includes a forceps shaft part 8 which supports the foregoing forceps tip assembly 1 and links the forceps tip assembly 1 with the foregoing forceps base part 2. The forceps shaft part 8 and the foregoing forceps base part 2, which is illustrated excluding a cover in FIG. 4, arm constituted so as to be easily separated from each other as described later. Thus, the forceps tip assembly 1 that touches an operated part can be always kept clean. Moreover, during a surgery, several kinds of forceps shaft parts 8 are prepared and appropriately replaced. Thus, forceps tips with different shapes can be used in accordance with operations.

FIG. 5*a* is a front view showing the forceps shaft part 8 together with the forceps tip assembly 1 and FIG. 5*b* is an end view when FIG. 5*a* is viewed from the rear end. An outer diameter of the forceps shaft part 8 is preferably made as thin as possible. However, since the forceps tip supporting member 3 of the forceps tip assembly 1 has a particular tripodal shape, the outer diameter is required to have a certain extent of thickness in order to secure rigidity thereof. Accordingly, in this embodiment, considering that the outer diameter is made as thin as possible within a range maintaining rigidity, the outer diameter of the forceps shaft part 8 is set to 10 mm as shown in FIGS. 5*a* and 5*b*. Moreover, assuming that the forceps shaft part 8 is inserted into the abdominal cavity by about 150 mm, a length of the forceps shaft part 8 is set so as to protrude from the forceps base part 2 by about 300 mm.

The forceps shaft part 8 has three linking members 8*a*, 8*b* and 8*c* disposed around a predetermined central axis line C3 coinciding with the central axis line C2 of the forceps tip assembly 1 at even intervals in a circumferential direction. Moreover, a rod 8*d* as a link to open and close a forceps tip is inserted into a center hole defined by the linking members 8*a* to 8*c*. Tip portions (left end portions in FIG. 5*a*) of the three linking members 8*a* to 8*c* are coupled with the back-and-forth moving members 4 to 6, respectively, to support those members. Root portions of the three linking members 8*a* to 8*c* and the rod 8*d* are inserted into a fixation sleeve 8*e* and the root portion of the linking member 8*a* thereamong is fixed to the fixation sleeve 8*e* without protruding from the fixation sleeve 8*e*. With the root portions of the two linking members 8*b* and 8*c* and the rod 8*d*, which penetrate the fixation sleeve 8*e* in a freely slidable manner and protrude therefrom, three engaging members 8*f*, 8*g* and 8*h* with a cross section of an approximately trapezoidal shape are coupled, respectively, which are disposed around the foregoing central axis line C3 at even intervals in the circumferential direction. The forceps base part 2 transmits a driving force via the forceps shaft part 8 as described later and slides the two engaging members 8*f* and 8*g* back and forth while fixing the fixation sleeve 8*e*. Thus, it becomes possible to realize two degrees of freedom of bending of the forceps tip supporting member 3 with high rigidity. Moreover, by sliding the engaging member 8*h* back and forth, it is possible to open/close the forceps tip with high rigidity.

Figure 6A:
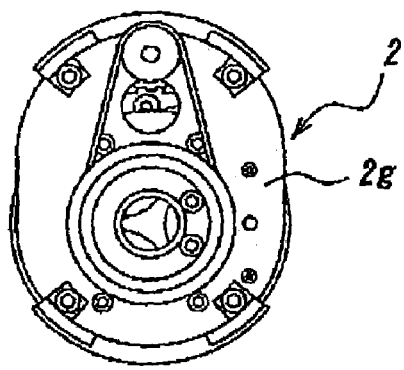
FIGS. 6a to 6c are plan, front and side views showing a forceps base part of the active forceps of the foregoing embodiment after removing a cover thereof.
Figure 6B:
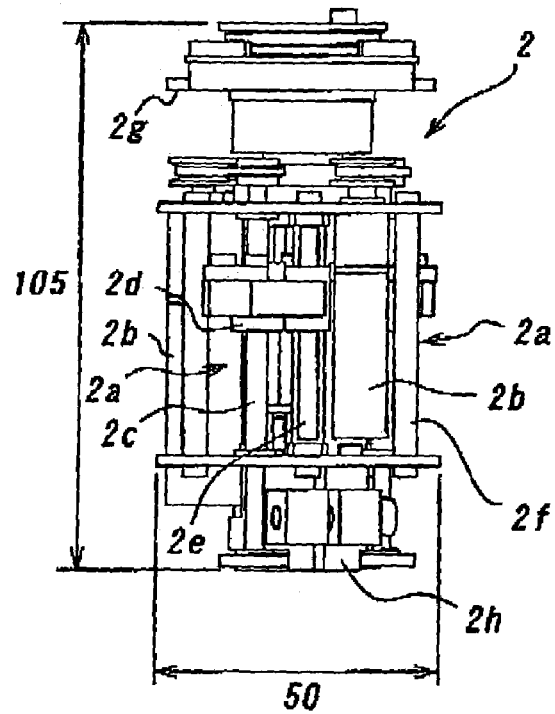
Figure 6C:
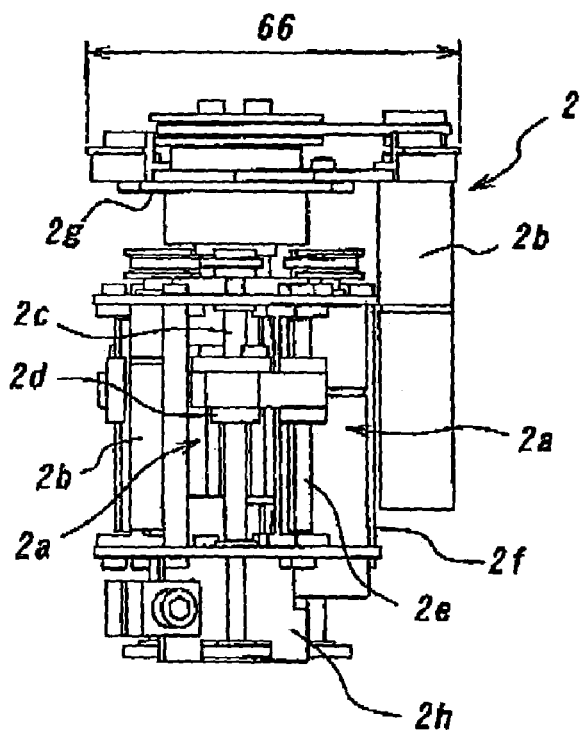

FIGS. 6*a*, 6*b* and 6*c* are plan, front and side views showing the foregoing forceps base part 2 with a cover removed therefrom. On the forceps base part 2 herein, four motors are mounted in total, including: two for back-and-forth movement of the back-and-forth moving members 5 and 6 via the two engaging members 8*f* and 8*g* and the two linking members 8*b* and 8*c*, one for opening/closing the forceps tip via the engaging member 8*h* and the rod 8*d*; and one for rotating the forceps tip assembly 1 and the forceps shaft part 8 around the foregoing central axis lines C2 and C3.

Specifically, the forceps base part 2 has three linear movement mechanisms 2*a* for the back-and-forth movement of the back-and-forth moving members 5 and 6 and for the opening/closing of the forceps tip. Each of these linear movement mechanisms 2a has a constitution in which a DC servo motor 2b rotates a ball screw 2c and a ball nut 2d screwed thereinto is moved back and forth while being guided by a linear guide 2e. The back-and-forth movement mechanism 2a for the back-and-forth moving members 5 and 6 as a driving mechanism includes: the 2.5 W DC servo motor 2b with reducer with a reduction gear ratio of 4.1:1; and the ball screw 2c with a pitch of 1 mm. Here, a frame 2f mounting these three back-and-forth movement mechanisms 2a disposed in parallel with each other is supported as capable of rotating by a bracket 2g and is rotated by the servo motor 2b with reducer for rotation as a whole. Accordingly, a clamp 2h for the fixation sleeve 8e fixedly installed in one end portion of the frame 2f (a lower end portion in FIGS. 6b and 6c) is rotated and thus the forceps tip assembly 1 and the forceps shaft 8 are rotated around the foregoing central axis lines C2 and C3. In this embodiment, these mechanism components are disposed closely to each other, so that a size of the forceps base part 2 is set to about 50 mm×66 mm×105 mm. Thus, miniaturization of the active forceps is realized. Moreover, assuming that the active forceps is held by a positioning robot for a surgical tool, which will be described later, during a surgery, magnesium alloy is used as a material for components of a main structure of the active forceps. Thus, a lighter active forceps is achieved.

FIGS. 7a to 7c am explanatory views showing a procedure of mounting the forceps shaft part 8 on the foregoing forceps base part 2. In an actual surgery, an operation is executed while replacing various surgical tools in accordance with a therapeutic situation and a state of the affected area. Thus, it is required that forceps part and driving part of the active forceps can be easily and rapidly attached to/detached from each other. Consequently, as shown in FIGS. 7a to 7c, in the active forceps of this embodiment, in order to meet such a requirement, three holders 2i as base part side back-and-forth moving members are fixedly installed on the ball nuts 2d of the three back-and-forth movement mechanisms 2a of the forceps base part. Specifically, the three holders 2i are coupled with each other via the frame 2f and are engaged with the engaging members 8f to 8h of the forceps shaft part 8, respectively.

Consequently, in mounting the forceps shaft part 8, as shown by the arrow D in FIG. 7a, the engaging members 8f to 8h of the forceps shaft part 8 are first inserted into an approximately triangular center hole defined by the three holders 2i from a lower side (a near side in FIG. 7a) of the forceps base part 2 which is usually used while allowing an end portion at the bracket 2g side to face upward. At the same time, the fixation sleeve 8e of the forceps shaft part 8 is inserted into the clamp 2h which is not illustrated herein. Next, as shown by the arrow B in FIG. 7b, the forceps shaft part 8 is rotated around the center axis line C2 by 60 degrees and the engaging members 8f to 8h are engaged with the three holders 2i, respectively. Lastly, as shown by the arrow F in FIG. 7c, a fasting screw 2j of the clamp 2h is fastened and thus the fixation sleeve 8e of the forceps shaft part 8 is held by the clamp 2h and fixed to the frame 2f. With such a simple procedure as described above, the forceps shaft part 8 can be easily mounted on the forceps base part 2. Moreover, with a reverse procedure to the above, the forceps shaft part 8 can be easily detached.

Note that the forceps tip assembly 1 and the forceps shaft part 8, which mount the forceps tip thereon, include no electric or electronic components and thus can be sterilized before a surgery. Consequently, the forceps tip that touches the affected area can be used in its clean state. The forceps base part 2 can also secure its cleanliness by mounting a cylindrical cover thereon as shown in FIG. 2.

Figure 8:
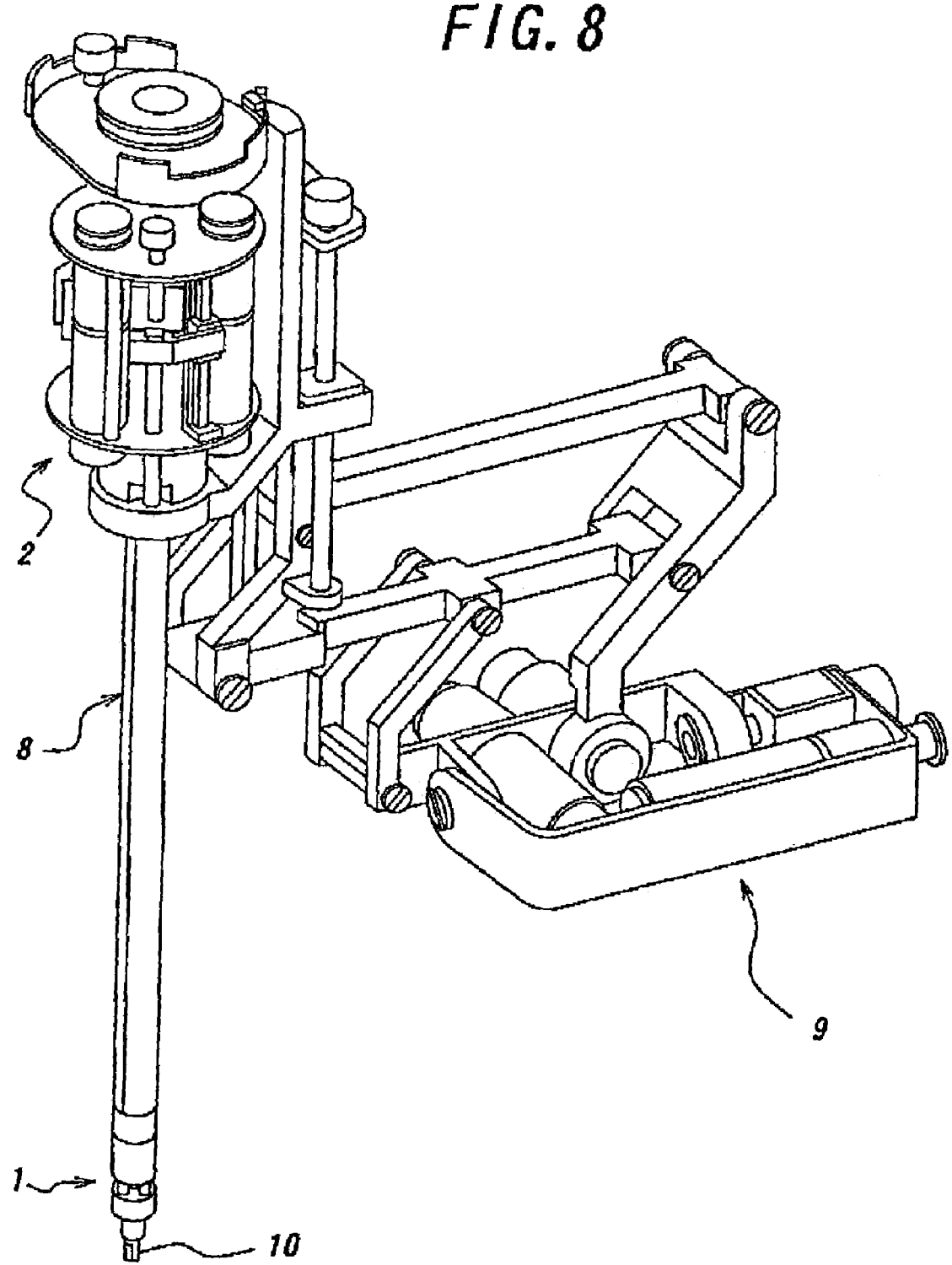
FIG. 8 is a perspective view showing a small-sized slave robot in which the active forceps of the foregoing embodiment is held by an active trocar.

FIG. 8 is a perspective view showing a small-sized slave robot in which the active forceps of the foregoing embodiment is held by an active trocar 9 developed as a positioning robot for a surgical tool. The active trocar 9 is a mechanism of determining three degrees of freedom in position of a tip of the held surgical tool by use of back-and-forth movement by a parallel link mechanism, left-and-right inclination by swinging of the entire parallel link mechanism and elevation by a ball screw linear movement mechanism similar to the back-and-forth movement mechanism 2a. Moreover, together with a mechanism of determining three degrees of freedom in posture of the supporting part 3a of the active forceps of the foregoing embodiment, the active trocar 9 can freely determine six degrees of freedom in position and posture of the forceps tip 10 in the abdominal cavity. For an arm for disposing this slave robot on an operated part, for example, a point setter can be used. The point setter is an articulated arm having a passive mechanism in which injection of compressed air enables a posture of the arm to be manually changed and discharging of the compressed air allows the arm to be fixed in the posture after the change. When a plurality of point setters is used, a plurality of slave robots can be provided in arbitrary positional postures on an abdominal wall of a patient. Thus, the point setter can be applied to various surgical techniques.

The present invention has been described above based on the examples shown in the drawings. However, the present invention is not limited to the above described examples. For example, the opening/closing of the forceps tip may be performed by driving the forceps tip by a wire, an electromagnetic solenoid or the like. Moreover, besides the one that opens and closes, the forceps tip may be one mounting a laser surgical knife or a camera.

What is claimed is:

1. A high-rigidity forceps tip assembly for an active forceps, comprising:
   a forceps tip supporting member having a supporting part for supporting a forceps tip, and only three leg parts which are positioned at even intervals in a circumferential direction around a central axis line of the supporting part and are fixed to the supporting part so as to protrude backward from the supporting part, respectively; and
   three back-and-forth moving members which are disposed at even intervals in a circumferential direction around a predetermined central axis line extending in a front-to-rear direction, which have their front end portions coupled with the only three leg parts swingably and slidably in a direction orthogonal to the predetermined central axis line and which are mutually coupled together as relatively movable in the front-to-rear direction.

2. The high-rigidity forceps tip assembly for an active forceps according to claim 1, wherein spheres formed in respective rear end portions of the three leg parts and cylindrical grooves which are formed in the respective front end portions of the three back-and-forth moving members and extend in the direction orthogonal to the predetermined central axis line are engaged with each other so as to be swingable and slidable, and by this swingable and slidable engagement, the three leg parts are coupled with the front end portions of the three back-and-forth moving members so as to be swingable and slidable in the direction orthogonal to the predetermined central axis line, respectively.

3. The high-rigidity forceps tip assembly for an active forceps according to claim 2, wherein the supporting part is formed of a ring-shaped member.

4. The high-rigidity forceps tip assembly for an active forceps according to claim 2, wherein the three back-and-forth moving members are coupled with each other as relatively movable in the front-to-rear direction by use of grooves and ribs which form a hook-shaped cross section, are engaged with each other so as to be slidable in the front-to-rear direction and are hooked up with each other in a direction intersecting with the front-to-rear direction.

5. An active forceps, comprising:
the high-rigidity forceps tip assembly for an active forceps according to claim 2; and
a forceps base part having three base part side back-and-forth moving members which are integrally coupled with the three back-and-forth moving members, are coupled with each other as relatively movable in the front-to-rear direction and constitute a link mechanism together with the back-and-forth moving members and the supporting part, and a base part frame including driving means for relatively moving the base part side back-and-forth moving members in the front-to-rear direction.

6. The high-rigidity forceps tip assembly for an active forceps according to claim 1, wherein the supporting part is formed of a ring-shaped member.

7. The high-rigidity forceps tip assembly for an active forceps according to claim 6, wherein the three back-and-forth moving members are coupled with each other as relatively movable in the front-to-rear direction by use of grooves and ribs which form a hook-shaped cross section, are engaged with each other so as to be slidable in the front-to-rear direction and are hooked up with each other in a direction intersecting with the front-to-rear direction.

8. An active forceps, comprising:
the high-rigidity forceps tip assembly for an active forceps according to claim 6; and
a forceps base part having three base part side back-and-forth moving members which are integrally coupled with the three back-and-forth moving members, are coupled with each other as relatively movable in the front-to-rear direction and constitute a link mechanism together with the back-and-forth moving members and the supporting part, and a base part frame including driving means for relatively moving the base part side back-and-forth moving members in the front-to-rear direction.

9. The high-rigidity forceps tip assembly for an active forceps according to claim 1, wherein the three back-and-forth moving members are coupled with each other as relatively movable in the front-to-rear direction by use of grooves and ribs which form a hook-shaped cross section, are engaged with each other so as to be slidable in the front-to-rear direction and are hooked up with each other in a direction intersecting with the front-to-rear direction.

10. An active forceps, comprising:
the high-rigidity forceps tip assembly for an active forceps according to claim 9; and
a forceps base part having three base part side back-and-forth moving members which are integrally coupled with the three back-and-forth moving members, are coupled with each other as relatively movable in the front-to-rear direction and constitute a link mechanism together with the back-and-forth moving members and the supporting part, and a base part frame including driving means for relatively moving the base part side back-and-forth moving members in the front-to-rear direction.

11. An active forceps, comprising:
the high-rigidity forceps tip assembly for an active forceps according to claim 1; and
a forceps base part having three base part side back-and-forth moving members which are integrally coupled with the three back-and-forth moving members, are coupled with each other as relatively movable in the front-to-rear direction and constitute a link mechanism together with the back-and-forth moving members and the supporting part, and a base part frame including driving means for relatively moving the base part side back-and-forth moving members in the front-to-rear direction.

\* \* \* \* \*